Figure 1:
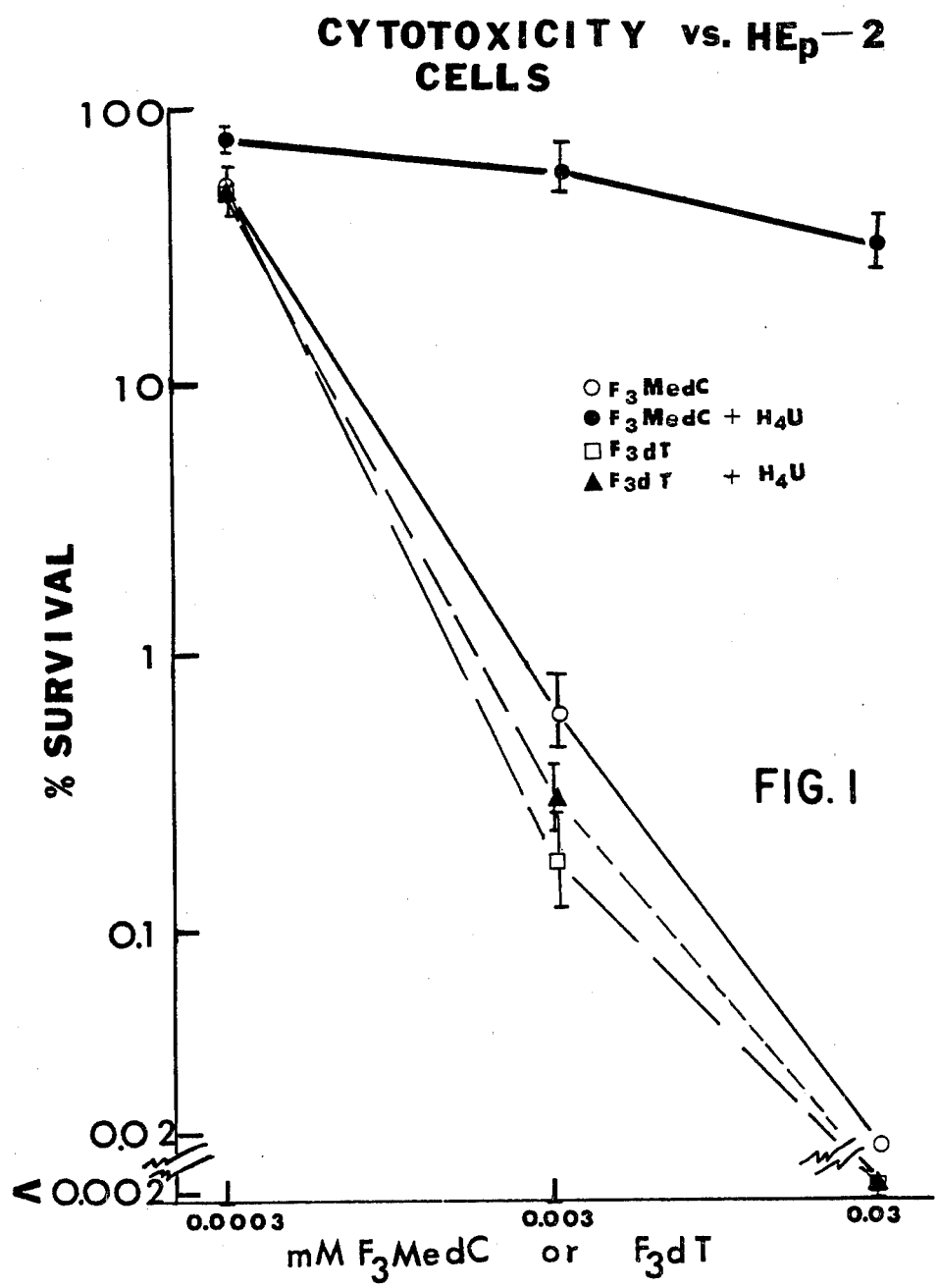

United States Patent [19]

Greer

[11] 4,210,638

[45] Jul. 1, 1980

[54] ANTIVIRAL COMPOSITION AND METHOD OF TREATING VIRUS DISEASES

[75] Inventor: Sheldon Greer, Miami, Fla.

[73] Assignees: PCR, Inc., Gainesville; University of Miami, Miami, both of Fla.

[21] Appl. No.: 887,541

[22] Filed: Mar. 17, 1978

[51] Int. Cl.² .................... A61K 31/70; C07H 17/00
[52] U.S. Cl. ..................................... 424/180; 536/23
[58] Field of Search .......................... 536/23; 424/180

[56] References Cited
U.S. PATENT DOCUMENTS

| | | | |
|---|---|---|---|
| 4,017,606 | 4/1977 | Hanze et al. | 424/180 |
| 4,086,417 | 4/1978 | Ishida et al. | 536/23 |

Primary Examiner—Johnnie R. Brown
Assistant Examiner—Blondel Hazel
Attorney, Agent, or Firm—Murray and Whisenhunt

[57] ABSTRACT

Pharmaceutical compositions suitable for the treatment of Herpes or Herpes-like viruses are disclosed, wherein the compositions contain 5-trifluoromethyl-2'-deoxycytidine and a cytidine deaminase inhibitor. Also disclosed are methods of treating patients suffering from a disease caused by a Herpes or Herpes-like virus, with the method comprising administering to the patient a therapeutically effective amount of 5-trifluoromethyl-2'-deoxycytidine and a cytidine deaminase inhibitor.

15 Claims, 3 Drawing Figures

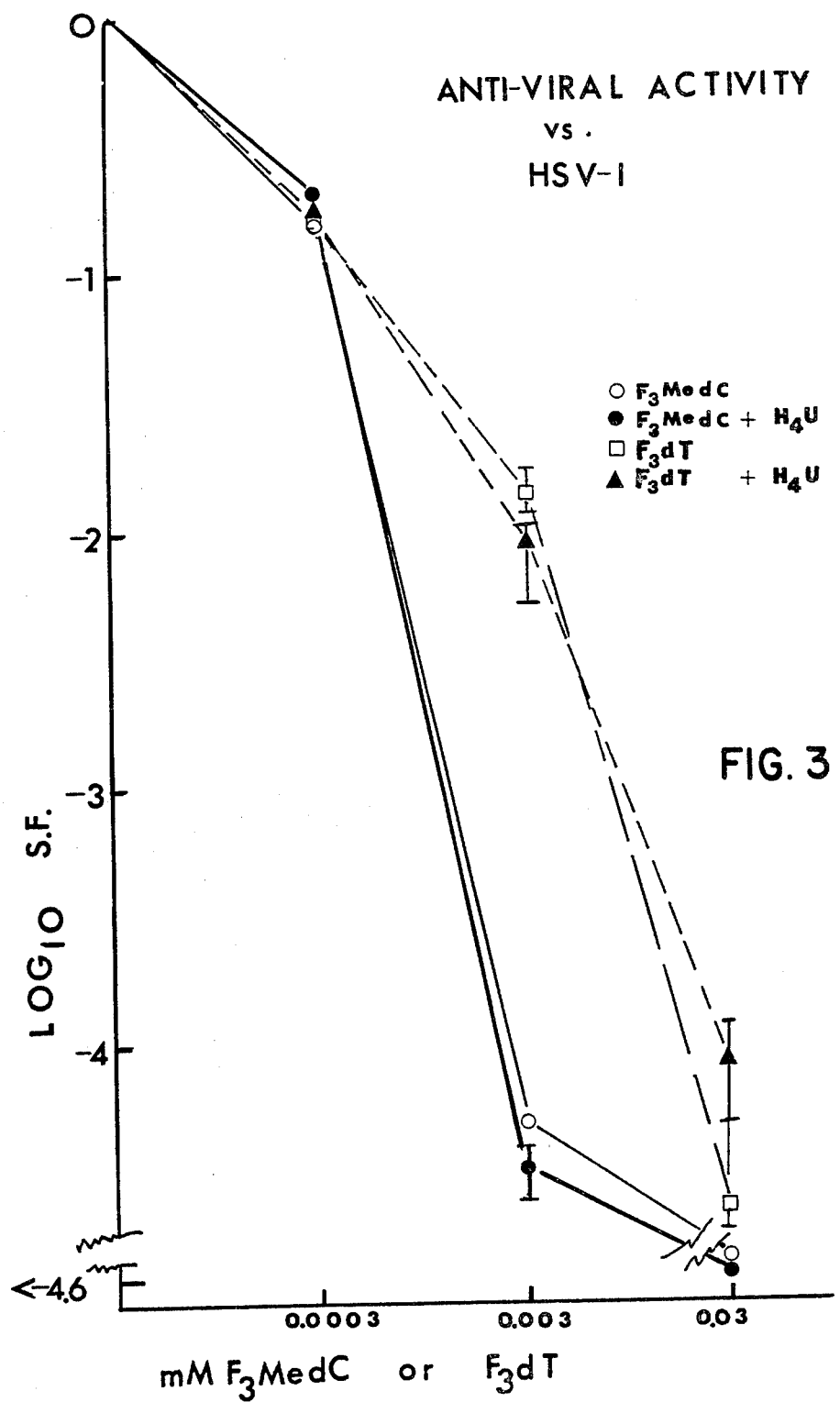

ANTIVIRAL COMPOSITION AND METHOD OF TREATING VIRUS DISEASES

BACKGROUND OF THE INVENTION

The present invention relates to pharmaceutical compositions containing 5-trifluoromethyl-2'-deoxycytidine and a cytidine deaminase inhibitor, and to a method for treating diseases caused by Herpes or Herpes-like virus by administering 5-trifluoromethyl-2'-deoxycytidine and a cytidine deaminase inhibitor.

Diseases caused by Herpes and Herpes-like viruses are particularly widespread in man. Examples of Herpes viruses are Herpes simplex virus (HSV) Types 1 (HSV-1) and 2 (HSV-2) and Herpes varicella-zoster virus (VZV) that causes chicken pox in children and shingles in adults. Other examples of Herpes-like viruses are Epstein-Barr virus, Pseudorabies virus, Cytomegalo virus, Marek's disease virus of chickens, equine abortion virus (EAV) and Lucke-frog virus.

Herpes simplex viruses are strongly implicated in many pathological systems and include ocular (Keratitis), cutaneous (including genital and oral), and systemic disseminated infections. One disease caused by the Herpes simplex virus Type 1 (HSV-1) is a particularly virulent form of encephalitis which, if not treated effectively, is usually fatal. Recurrent and persistent genital infections occur with HSV-2 that are widespread in the population and defy management so that these patients suffer great physical discomfort and psychological distress. HSV-1 causes substantial discomfort to a large segment of the population. There is at this time no known way to manage recurrent infections or to combat this virus in its latent stage.

Varicella-zoster is often the cause of morbidity in immunosuppressed patients such as kidney transplant recipients. Cytomegalo virus causes embryological abnormalities, perinatal neurological disease and great problems in the neonate; like zoster, it is a neurotropic virus.

An extremely active area of the current medical research is the study of virus caused diseases, in particular those induced by Herpes and Herpes-like viruses. An important part of this research is the development of selective antiviral agents for the treatment of these diseases. As will be discussed in more detail below, the major problem with the antiviral agents presently available is their tendency to undergo catabolism in the body and, more importantly, their toxicity towards uninfected cells; that is, their nonselectivity.

The search for effective antiviral agents which exhibit specific antiviral activity against cells infected with Herpes and Herpes-like viruses has met with varying degrees of success. In 1962, Kaufman (IDU Therapy of Herpes Simplex, Arch. Ophthalmol. 67, 583, 1962) investigated the antiviral activity of certain 5-halo-deoxyuridine compounds and found tht 5-iodo-2'-deoxyuridine (IdU) exhibits antiviral activity against HSV infections of the eye. Subsequently, Heidelberger discovered that, while 5-fluorodeoxyuridine exhibits very little antiviral activity, 5-trifluoromethyl-2'-deoxyuridine, or 5-trifluoro thymidine ($F_3dT$), does exhibit antiviral activity against infections of the eye. The compound $F_3dT$ is described and claimed in U.S. Pat. No. 3,201,387.

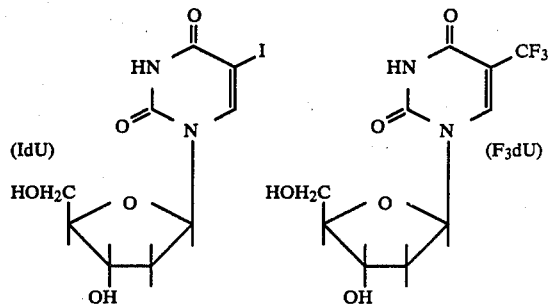

Although IdU is effective against Herpes Keratitis it is less effective than $F_3dT$ and is not as effective in systemic infections or in the treatment of Herpes genitalis.

Despite exhibiting antiviral activity, these two compounds (IdU and $F_3dT$) suffer from two major disadvantages. The first is that the compounds undergo rapid catabolism in the body which results in significant reduction of antiviral effectiveness of the compound. The second disadvantage is that the compounds exhibit toxicity towards uninfected cells which, in turn, results in the generation of unpleasant and harmful side effects. IdU has been abandoned for the treatment of Herpes encephalitis because of its toxicity and its ineffectiveness, and $F_3dT$ has not been considered for the treatment of systemic infections. There are some approaches that involve direct intracranial injection of this compound for the treatment of encephalitis; however, the studies are still at the stage of animal models. Furthermore, the approach to treatment appears to be associated with potential hazards for use in humans.

Studies on various 5-substituted analogs of deoxyuridine, including 5-methyl amino-2'-deoxyuridine, 5-thiocyanato-2'-deoxyuridine, 5-ethyl-2'-deoxyuridine, 5-propyl-2'-deoxyuridine, 5-phenyl-2'-deoxyuridine and 5-allyl-2'-deoxyuridine have been reported which indicate that these compounds do exhibit antiviral activity against Herpes simplex in cell culture; however, the success of these compounds will likely remain limited to cell culture studies, in spite of the fact that they are non-toxic in culture, for they are substrates for the catabolic enzymes uridine and thymidine phosphorylase.

Adenine arabinoside has been shown to decrease the incidence of death due to human encephalitis. However, the number of individuals with neurological sequelae was discouraging. That is, the drug decreased the mortality but increased the morbidity. Furthermore, ara-A or ara-AMP is neither effective against recurrent genital Herpes nor does it decrease the incidence of latent virus infection. Phosphonacetic acid is effective in animal systems; however it must be administered in most cases very soon after infection, and is usually ineffective if the onset of treatment is delayed to coincide with realistic intervals for consideration for use in humans.

Other drugs such as ara-T, 4-amino-5-iodo-deoxyuridine and acycloguanine are in various stages of development and are far from being ready for use in clinical studies. Furthermore, in view of the capacity of viruses to mutate to resistance to a drug (as is the case with phosphonacetic acid) it is likely that ultimately viral chemotherapy will involve a combination of drugs that act via different mechanisms.

More recently, attention has turned to the study of deoxycytidine compounds as possible antiviral agents and, in particular, the 5-substituted analogs thereof. Greer et al. (Annals of the New York Academy of Sciences, Volume 255, 359, 1975) have studied the antiviral activity of 5-halo-2'-deoxycytidines, namely 5-bromo-2'-deoxycytidine (BrdC) and 5-iodo-2'-deoxycytidine (IdC). The studies have shown that these 5-halo-2'-deoxycytidine compounds possess a similar antiviral activity against HSV infected cells as that possessed by the corresponding 5-halo-2'-deoxyuridine compounds, but most importantly that the 5-halo-2'-deoxycytidine compounds are substantially less toxic towards uninfected cells than the deoxyuridine compounds. Kurimoto et al. Folia. Ophthalmol. Japan, 20, 49 (1969) have shown that IdC is more effective in the treatment of Herpes Keratitis in humans than IdU.

A drawback of the 5-halo-2'-deoxycytidine compounds is their tendency to undergo deamination in the presence of deaminating enzymes, such as cytidine deaminase. Such enzymes are usually present in the blood and catalyze the deamination of the 5-halo-2'-deoxycytidine compound to the corresponding 5-halo-2'-deoxyuridine compound. As a result of this deamination, uridine compounds are formed which do not display selectivity and which exhibit toxicity towards uninfected cells and generate unpleasant and harmful side effects. Furthermore, deoxyuridine analogs are further degraded to metabolites that do not display antiviral activity.

In order to overcome this problem of deamination, it has been found necessary to employ a deamination inhibitor, and tetrahydrouridine ($H_4U$) and 2'-deoxytetrahydrouridine ($H_4dU$) have been found particularly suitable for this purpose. These two compounds are described in U.S. Pat. No. 4,017,606 (Hanze et al.). The patent describes the synthesis of $H_4U$ and $H_4dU$ starting from a compound whose general formula covers the compound 5-trifluoromethyl-2'-deoxycytidine($F_3$methyl dC) which forms the subject of the present invention. However, there is no specific disclosure of $F_3$methyl dC in the Hanze et al. patent and there is no disclosure of any utility of $F_3$methyl dC as an antiviral agent.

Studies have been recently reported of the antiviral activity of 5-methyl-2'-deoxycytidine and 5-ethyl-2'-deoxycytidine. Shugar (J. Med. Chem., Vol. 17, No. 3, 296, 1974) discovered that 5-ethyl-2'-deoxycytidine possesses only a low antiviral activity against HSV infected cells and no activity against vaccinia and vesicular stomatitis. Very recent studies by Lin and Prusoff (Abstracts of Papers, 174th ACS Meeting, American Chemical Society, Aug. 28–Sept. 2, 1977) have shown that 5-methyl-2'-deoxycytidine is less effective as an antiviral agent against HSV infected cells than 5-methyl-2'-deoxyuridine.

SUMMARY OF THE INVENTION

The compound 5-trifluoromethyl-2'-doxycytidine (also called $F_3$methyl dC) having the formula:

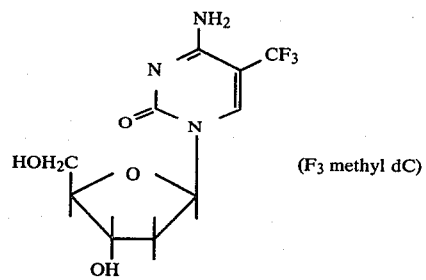

($F_3$ methyl dC)

exhibits several surprising and unexpected advantages over the prior antiviral agents discussed above. In particular, the compound $F_3$methyl dC exhibits an increased specificity towards cells infected with Herpes and Herpes-like viruses. It is not anabolized to a cytotoxic metabolite in uninfected cells. Furthermore, $F_3$methyl dC shows a substantially increased metabolic stability which results in a sustained antiviral activity. The compound exhibits a substantially pronounced antiviral activity at non-cytotoxic concentrations.

5-trifluoromethyl-2'-deoxycytidine is prepared by reacting 5-trifluoromethyl-2'-deoxyuridine ($F_3dU$), in which the free hydroxy groups have been protected, with ammonia. The reaction is generally carried out at an elevated temperature which does not exceed the decomposition temperatures of the starting materials or the end products. The reaction temperature can generally vary from about 50° C. to 250° C., and preferably from about 60° C. to 100° C. It has been found in practice that temperatures of about 60° C. to 80° C. give most satisfactory results. The precise temperature at which the reaction is carried out will, of course, depend on the nature of the reactants and the solvents employed, and the most appropriate temperature can be readily determined by routine experimentation.

It is generally necessary to protect the free hydroxy groups before amination will proceed satisfactorily. It is possible to employ any suitable protecting group, although for ease of handling it is generally preferred to use a blocking or protecting group which produces a crystalline rather than a liquid product. It has been found that synthesis proceeds most satisfactorily using a silyl protecting group such as the trimethylsilyl group, which can be introduced according to the procedure described by Vorbrüggen and Niedballa, Angew. Chem. Internat. Edit. Volume 10, No. 9, 657 (1971), the disclosure of which is hereby incorporated by reference. Thus, the reaction is preferably carried out by reacting 5-trifluoromethyl-2'-deoxyuridine ($F_3dU$) with a silylating agent such as hexamethyldisilazane (HMDS) or trimethylsilylchloride (trimethylchlorosilane or TMCS) in the presence of excess ammonia. The silylating agent is usually employed in an excess and serves as a solvent for the reaction as well as the silylating agent. It is also possible to use different protecting groups on different free hydroxy groups. For instance, the 2,4-positions of the pyrimidine ring can be protected by reaction with one type of protecting group agent, and the hydroxy groups on the deoxyfuranosyl ring can be protected by use of a different protecting group.

The reaction is usually carried out for at least ten hours, more usually twenty to fifty hours. It is not essential to conduct the reaction under superatmospheric pressure, but it has been found advantageous to conduct the reaction in a sealed tube or in an autoclave to avoid undue loss of ammonia during the heating process. When the reaction is carried out in an autoclave or sealed tube, pressures of 50-200 psi, more preferably 60-80 psi, have resulted in good yields of the desired compound F$_3$methyl dC.

When the reaction is completed, the resulting reaction mixture is usually an oily brown liquid which can be worked up according to conventional techniques to yield the desired compound F$_3$methyl dC as a white crystalline solid. The compound F$_3$methyl dC is insoluble in acetone and partially soluble in water, and can be satisfactorily recrystallized from hot water.

A surprising and unexpected feature of the preparation is the stability of the CF$_3$ group under the reaction conditions. The literature teaches that heating 5-trifluoromethyl-2'-deoxy-3',5'-di-O-toluyluridine with methanolic ammonia in a steel bomb at about 100° C. forms entirely the 5-carbomethoxynucleoside (Ryan et al., J. Org. Chem., 31, 1181 (1966). It is possible that the presence of a protecting group in the pyrimidine ring changes the course of the reaction.

Another surprising and unexpected feature of the preparation of F$_3$methyl dC is that the silylation/amination reaction does not proceed in the absence of an N$_1$-substituent. Thus, reaction of 5-trifluoromethyluracil with HMDS and excess ammonia according to the reaction conditions described above does not yield the corresponding amine compound, as illustrated by Comparative Example A hereinbelow.

The starting compound, 5-trifluoromethyl-2'-deoxyuridine (trifluorothymidine) can be prepared by procedures such as those described in Heidelberger et al., J. Am. Chem. Soc., 34, 3597 (1962) and J. Med. Chem., 7, 1 (1964) and U.S. Pat. No. 3,201,387, and Ryan et al., J. Org. Chem., 31, 1181 (1966).

In the silylation reaction described above, it has been found that a mixture of HMDS and a small amount of TMCS will produce a higher yield or faster reaction, as apparently a small amount of TMCS produces a catalytic effect. This effect is disclosed in U.S. Pat. No. 4,024,143, issued May 17, 1977, the disclosure of which is hereby incorporated by reference for the teaching of silylation reactions therein.

The preferred silylating agents have been described hereinabove. Broadly speaking, the silylation reaction can be conducted using at least a stoichiometric amount of a silylating agent which is:

silane of the formula

wherein R' is lower alkyl and X is halogen, and/or disilazane of the formula

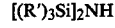

wherein R' is lower alkyl
at a temperature of about room temperature to the boiling point of the reaction mixture. The lower alkyl groups of the above formulae can contain from 1 to about 4 carbon atoms.

The authenticity of the compound of the present invention is established by the following procedure wherein F$_3$dT is trifluorothymidine (5-trifluoromethyl-2'-deoxyuridine).

F$_3$dT (R$_f$=0.43) and F$_3$methyl dC (R$_f$=0.80) are separable in a chromatography system consisting of Whatman 3MM and H$_2$O saturated n-butanol-NH$_3$ (100 ml H$_2$O saturated n-butanol+1 ml concentrated NH$_4$OH). Incubation of F$_3$methyl dC with a crude source of cytidine deaminase extract of human epidermoid carcinoma (HEP-2 cells) resulted in the formation of an R$_f$=0.43 spot and disappearance of the 0.80 spot on the above chromatography system. F$_3$dT incubated with cytidine deaminase remained unchanged chromatographically.

The results of incubation with HNO$_2$ (pH 4.5) at room temperature were identical to those obtained above. Incubation of F$_3$methyl dC for 9 hours resulted in approximately 98% conversion to a product that has the same R$_f$ as F$_3$dT in the same solvent system described above. F$_3$dT remained unaltered. Incubation of F$_3$methyl dC and F$_3$dT with an acetate buffer (pH 4.5) for 9 hours did not lead to modification of the deoxyribonucleosides.

The following spots were eluted into H$_2$O and scanned from 225 to 350 nm: (a) standard, (b) F$_3$methyl dC standard, (d) R$_f$=0.43 spot after cytidine deaminase treatment of F$_3$dT and (d) R$_f$=0.43 spot after cytidine deaminase treatment of F$_3$methyl dC. The u.v. absorption profile of F$_3$dT derived from deamination of F$_3$methyl dC is identical to that obtained from authentic F$_3$dT.

Solutions a, c, and d, above, were adjusted to the same O. D. and used as substrates for HSV-2 induced pyrimidine deoxyribonucleoside kinase. Results:

| SOLUTION | nmoles phosphorylated/60min. |
|---|---|
| a | 0.07 |
| c | 0.08 |
| d | 0.05 |

Thus, the product of cytidine deaminase treatment of F$_3$methyl dC (d) was phosphorylated to the same extent as F$_3$dT.

Stock solutions of F$_3$dT and F$_3$methyl dC were made up and adjusted to the same concentration as the F$_3$dT and F$_3$methyl dC purified chromatographically (solutions a and b, respectively). Usually, F$_3$methyl dC is phosphorylated 1/6 of the extent that F$_3$dT is phosphorylated. This experiment was performed to determine if the chromatographic purification of F$_3$methyl dC described above resulted in better phosphorylation relative to F$_3$dT. This experiment was performed twice. Results:

|  |  | nmoles phosporylated/4 hrs | |
|---|---|---|---|
| Standard | F$_3$dT | 0.48 | (0.57 |
| Solutions | F$_3$methyl dC | 0.48 | (0.08) Approx 1 |
|  |  | | no significant difference in ratios |
| Chromatog. | F$_3$dT | 0.16 | (0.19) |
| purified | F$_3$methyl dC | 0.04 | (0.06) Approx ½ to ¼ |

Values for chromatographically purified samples are probably lower due to impurities arising from non-acid washed paper.

Other chromatographic systems and chemical analysis, including thin-layer chromatography, can be utilized to confirm the authenticity of the compound. The state of purity of the compound tested in the determinations described above was approximately 80%.

The analysis for C$_{10}$H$_{12}$F$_3$N$_3$O$_4$ was as follows:

Calculated: C 40.67; H 4.06; N 14.23; Found: C 40.63; H 3.80; N 13.08.

F$_3$methyl dC exhibits surprisingly selective antiviral activity, particularly against cells infected with HSV-1 and HSV-2 viruses, as well as against cells infected with Herpes-varicella-zoster virus (VZV). Further, F$_3$methyl dC exhibits a surprising and unexpected increase in metabolic stability which results in low cell cytotoxicity, when used in connection with a cytidine deaminase inhibitor, such as tetrahydrouridine, as compared to other compounds, such as trifluorothymidine, used with or without an inhibitor. The combination of high antiviral activity and low cell cytotoxicity results in the ability of F$_3$methyl dC to be used in such low amounts, while still retaining effective antiviral activity, that the cytotoxicity towards uninfected cells is minimized.

Because transformed cells express the Herpes encoded enzyme activity and are selectively sensitive to F$_3$methyl dC, it is expected that F$_3$methyl dC will possess the capacity to affect latent infections which are severe problems that involve the neurotropic aspects of these viruses.

F$_3$methyl dC may be formulated into pharmaceutical compositions comprising, as the principal active ingredient, pharmaceutically effective amounts of F$_3$methyl dC together with a pharmaceutically acceptable carrier or diluent, for intraperitoneal administration for animal studies, intravenous, subcutaneous, intramuscular, oral or topical administration. The concentration of the compound in the composition may vary from about 0.01 to 50% by weight depending on the route of administration, the frequency of administration, the severity of the condition, the age, weight and general physical condition of the patent being treated. When the composition is in the form suitable for topical administration, for example a cream, the concentration of F$_3$methyl dC will generally vary from about 5 to 50 wt.%, preferably about 5 to 20 wt.%, more preferably from about 5 to 10 wt.%. When the composition is in the form suitable for intraperitoneal administration for animal studies, for example, an aqueous solution of F$_3$methyl dC, the concentration of F$_3$methyl dC will generally vary from about 0.5 to 5% w/v, more usually about 1% w/v. For oral administration, the concentration of F$_3$methyl dC will generally be from 0.05 to 10 wt.%, preferably about 0.5 to 5 wt.%, and more preferably about 1 to 2 wt.%.

When F$_3$methyl dC is used for intravenous injection, the concentration of the compound will vary from about 0.05 to about 5% w/v, preferably about 0.1 to about 0.5% w/v. For intramuscular injection, the same concentrations as described above for the intraperitoneal mode of administration will be utilized. Furthermore, in certain instances, such as for certain types of encephalitis, intracranial injection may be utilized.

Other methods of administration may also be used. Suppositories may be used for certain types of viral infections, and it is possible that for some applications the F$_3$methyl dC will be administered in the form of slow-release surgical implants.

The pharmaceutically acceptable carrier or diluent employed in the compositions of the present invention may be any compatible non-toxic material suited for mixing with the active compound F$_3$methyl dC. When the composition is in a form suitable for parenteral use, for example intramuscularly or intravenously, the carrier which preferably is an aqueous vehicle, may also contain other conventional additives, such as a suspending agent for example methyl cellulose or polyvinylpyrrolidone (PVP), and a conventional surfactant. For oral administration, the compositions can be formulated as aqueous solutions, suspensions, capsules or tablets, suitably containing appropriate carriers or diluents, for example lactose, starch and/or magnesium stearate. In certain instances, increased antiviral activity may be obtained by coadministration of DMSO, which is also a solvent for the F$_3$methyl dC.

In order to inhibit the deaminating effect of enzymes such as cytosine deaminase, with the consequent reduction in antiviral activity, it is necessary for antiviral uses to coadminister either previously or with the compound F$_3$methyl dC, a deamination inhibiting agent, such as tetrahydrouridine (H$_4$U) or 2'-deoxytetrahydrouridine (H$_4$dU). Thus, the antiviral pharmaceutical compositions comprise (as the principal active ingredient) a pharmaceutically effective amount of F$_3$methyl dC, together with inhibiting amounts of a cytidine deaminase inhibitor, for example, tetrahydrouridine or 2'-deoxytetrahydrouridine. A pharmaceutically acceptable carrier or diluent such as described above is generally present, depending on the nature of the composition. Tetrahydrouridine and 2'-deoxytetrahydrouridine are not toxic in man at extremely high concentrations. Furthermore, they are relatively metabolically stable. The weight ratio of tetrahydrouridine or 2'-deoxytetrahydrouridine to F$_3$methyl dC can be 500:1 to 1:1, but more usually will be about 20:1 to about 5:1.

To determine the toxicity of F$_3$methyl dC or other antiviral agents to uninfected cells, non-confluent cultures of human epidermoid laryngeal carcinoma (HEp-2) cells were treated with nucleoside analogs at varying concentrations for 48 hours, at which time the monolayer of cells is washed with phosphate buffered saline in order to remove any residual analogs. The cells are then trypsinized to remove them from the culture dishes and are replated at various dilutions. At 7 days the cultures are stained and colonies of 50 cells or greater are counted as one viable cell. Viability, which is a valid parameter of toxicity is thus determined by replating the cells. Therefore, toxicity is measured in terms of cellular replication: colony formation.

FIG. 1 indicates the cytotoxicity of F$_3$methyl dC and F$_3$dT and without H$_4$U against HEp-2 cells (see Table I for similar data for F$_3$methyl dC). The dramatic enhancement of survival that is obtained when cells are grown in F$_3$methyl dC and H$_4$U will be readily noted.

To demonstrate inhibition of viral replication, HSV types 1 or 2 are adsorbed to HEp-2 cells at low multiplicities for two hours at 37° C. The culture medium containing the nucleoside analogs at varying concentrations are added to the infected cultures. In the case of HEp-2 cells which contain high deaminase levels, H$_4$U is incorporated into the medium. At 48 hours, virus is harvested from the cultures by freezing and thawing. The virus produced from each culture is titred by plaque assay in BHK cells. By using this protocol the antiviral effectiveness of F$_3$methyl dC can be compared directly with the effectiveness of other antiviral agents. Furthermore, by including H$_4$U in the medium, the effectiveness of F$_3$methyl dC can be determined without deamination at the nucleoside level.

Figure 2:
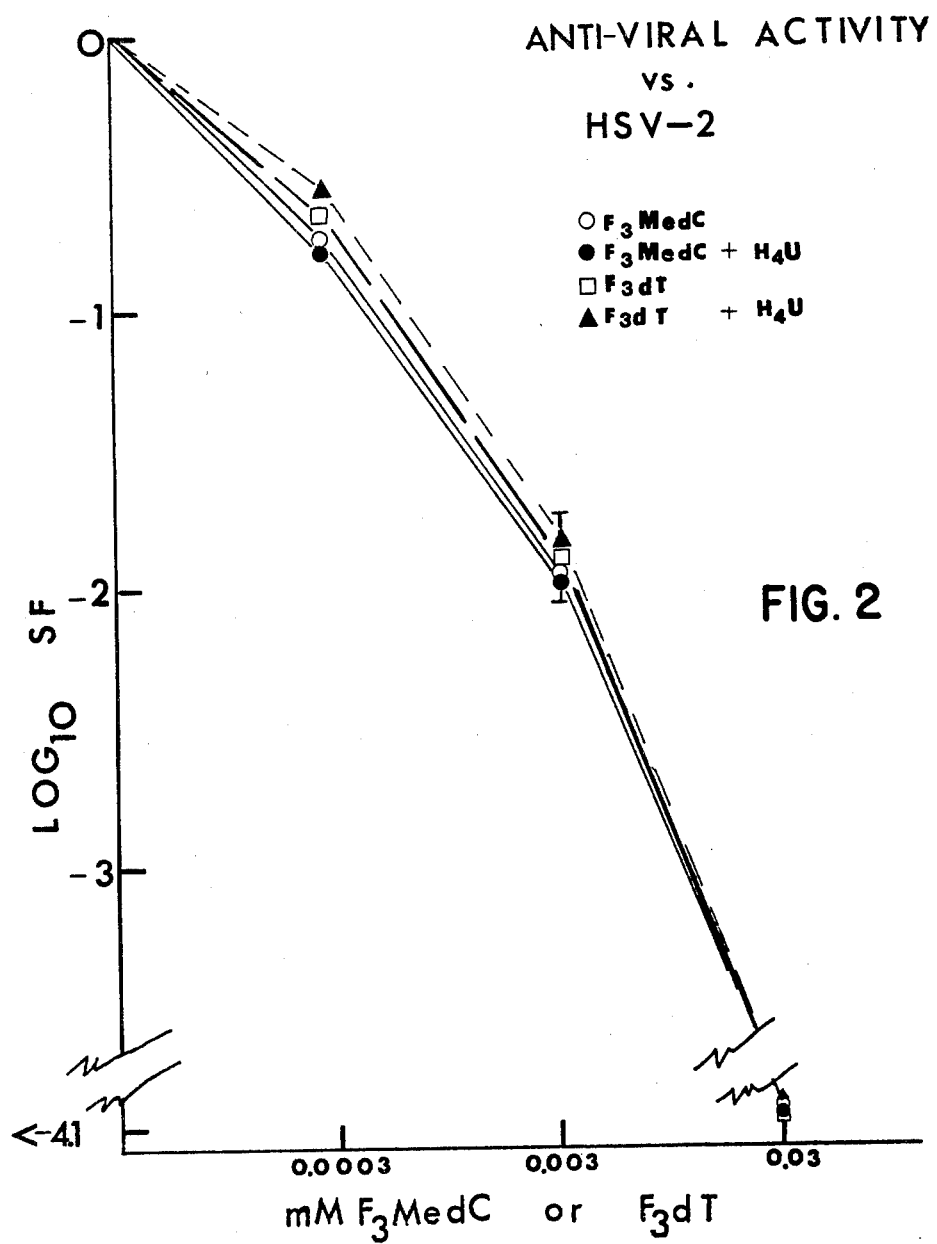

FIG. 2 demonstrates the antiviral activity of F$_3$methyl dC and F$_3$dT, with and without H$_4$U against HSV-2. The results indicate that the compounds are equally potent antiviral agents. An examination of Table II or a comparison with FIG. 1, however, reveals that F$_3$methyl dC (+H$_4$U) is only marginally cytotoxic at concentrations that possess effective antiviral activity, whereas F$_3$methyl dC (without H$_4$U) and F$_3$dT±H$_4$U are extremely cytotoxic concentrations at which they display antiviral activity. This then indicates a high therapeutic index for F$_3$methyl dC and H$_4$U.

Table III indicates that when cells are grown on F$_3$ methyl dC about a 5-fold increased survival can be obtained with the use of 2'-deoxytetrahydrouridine (H$_4$dU) than with H$_4$U without impairing the effectiveness of the antiviral activity of F$_3$methyl dC vs. HSV-2.

FIG. 3 indicates the antiviral activity of F$_3$methyl dC and F$_3$dT with and without H$_4$U vs. HSV-1. Note that F$_3$methyl dC ±H$_4$U displays more potent antiviral activity than F$_3$dT±H$_4$U.

A summary of the cogent data is shown in Table IV. F$_3$methyl dC±H$_4$U is an effective antiviral agent at concentrations that display marginal to only moderate cytotoxicity.

Animal patients, including humans, suffering from diseases caused by Herpes and Herpes-like viruses can be treated by administering to the patient a pharmaceutically effective amount of F$_3$methyl dC preferably in the presence of an deamination inhibitor and optionally, but preferably in the presence of a pharmaceutically acceptable carrier or diluent.

For the treatment of systemic infections, the F$_3$methyl dC of the present invention will preferably be administered by intravenous injection and less likely, but possibly, by oral administration. For the case of topical infection, the F$_3$methyl dC will most likely be administered topically.

It has been found that particularly advantageous results are obtained when the dosage of the compound F$_3$methyl dC to the patient is from about 0.01 mmoles/kg to 0.25 mmoles/kg per day for 7 days. That is, 3 mg/kg body weight to 75 mg/kg body weight; for example, about 10 mg/kg body weight per day for 7 days or 700 mg for a 70 kg man per day for 7 days. These projections are based on studies with the mouse in which it was found that a 60% survival was obtained with 250 mg F$_3$methyl dC per kg once per day for 7 days with H$_4$U coadministered one hour prior to the F$_3$methyl dC. 100 percent survival was obtained with a dose of 50 mg. F$_3$methyl dC per kg/day for 7 days when it was coadministered with H$_4$U. The LD$_{50}$ for F$_3$methyl dC (coadministered with H$_4$U) was 325 mg/kg/day for 7 days.

Although the discussion above is centered on the compound F$_3$methyl dC, it will be appreciated that other analogs containing a perfluorinated lower alkyl or lower alkenyl group in the 5-position, for example, 5-pentafluoroethyl-2'-deoxycytidine and 5-trifluorovinyl-2'-deoxycytidine, may exhibit similar antiviral and chemotherapeutic activity. In addition, 2',3'-dideoxy F$_3$methyl cytidine may be a selective DNA chain terminator for Herpes infected cells and the arabinosides 5-F$_3$ thymine arabinoside and 5-F$_3$ methylcytosine arabinoside may also be used. In addition, there may be potential efficacy in 2'-azido-5-F$_3$methyl dC for such uses.

EXAMPLES OF THE INVENTION

The present invention is further illustrated by the following non-limiting Examples, wherein percentages are by weight unless otherwise noted.

EXAMPLE I—Synthesis of F$_3$methyl dC

A mixture of 5-trifluoromethyl-2'-deoxyuridine (F$_3$dU) (10 g; 0.034 mole), hexamethyldisilazane (HMDS), (100 g) and ammonium chloride (0.01 g) was saturated with ammonia and heated at 150° C. overnight in a 500-ml Fischer-Porter aerosol compatibility tube. A light brown clear solution was obtained and the heating was continued for a further 24 hours. After a total of 44 hours, the heating was stopped and a clear brown solution was obtained. The solvent was removed under partial vacuum using a rotary evaporator at about 50° to 60° C. The residue was refluxed with methanol (150 ml) for about 6 hours. The methanol was removed using a rotary evaporator to give a solid (about 10 g). The solid was dissolved in boiling water (250 ml), filtered and cooled, giving a crystalline solid (2 g). Further crystals were deposited from the mother liquor which were isolated and shown to be the same as the crystals obtained earlier. The combined crystals were refluxed in ethanol (30 ml) to give the desired compound F$_3$methyl dC.

| Elemental Analysis | C | H | N |
|---|---|---|---|
| Actual | 40.31 | 4.46 | 13.70 |
| Theoretical | 40.67 | 4.06 | 14.23 |

U.V. Data

| | | |
|---|---|---|
| λ (0.1 HCl) (max) | = 282 | m μ (E = 10, 410) |
| λ (0.1 NaOH) (max) | = 279 | m μ (E = 10, 280) |

I.R. Data 3200 (broad), 1650 (broad), 1160, 1100, 1060 cm$^{-1}$

EXAMPLE II

The experiment of Example I was repeated as follows using a mixture of HMDS and trimethylsilyl chloride (TMCS) as a silylating agent. A mixture of F$_3$dU (5 g), HMDS (50 ml) and TMCS (0.2 ml) in a 100 ml autoclave was saturated with ammonia (10 g) at room temperature. A slight pressure of 10–20 psi was recorded. The mixture was then heated at about 165° C. for about 48 hours with a recorded pressure of about 200 psi. The autoclave was then opened and the resulting mixture was poured into a 50-ml flask. The solvent was removed under vacuum leaving a brown viscous liquid. Thin layer chromatography using a water solution indicated that only a trace of the starting materials remained and that the major component of the mixture was a different compound. The mixture was extracted with boiling water (200 ml), decolorized with charcoal, and filtered. The water was removed under vacuum using a rotary evaporator to give about 0.15 to 0.2 g of a compound which was shown by analysis to be the same compound as obtained in Example I.

EXAMPLE III

The procedure of Example II was repeated except that the reaction was performed in a sealed tube instead of an autoclave. A mixture of F$_3$dU (3.0 g) and HMDS (2.8 g) was placed in a Fischer-Porter tube and saturated with ammonia for about 30 minutes. A gel was formed. Then trimethylsilyl chloride (0.2 ml) was added to the mixture, and the tube was sealed and heated to 140° C. overnight, giving a pressure of 60 psi. The temperature was then increased to 150° C. giving a pressure of 80 psi. The heating was continued for a further 24 hours. A clear light brown solution was obtained and some solid had sublimed onto the cooler parts of the tube. The tube was cooled and some solid precipitated. The tube was opened and cooled and the HMDS was removed under vacuum at 50° to 60° C. leaving a viscous brown residue. Methanol (50 ml) was added and the mixture was heated to 65° to 70° C. for 6 hours. The methanol was then removed under vacuum leaving a brown solid which was dissolved in hot water (200 ml) and filtered. The filtrate was decolorized with charcoal, filtered and evaporated to dryness, giving a solid (2.5 g). This solid was dissolved in boiling water, filtered and cooled, yielding crystals (0.1 g) which were shown by analysis to be the same compound as obtained in Examples I and II.

EXAMPLE IV

An aqueous solution of the compound $F_3$methyl dC was prepared by dissolving $F_3$methyl dC (about 0.2 gm) in physiologically pure water (5 ml) under sterile conditions. The solution which was suitable for administration by injection, was then sealed in ampoules and stored, ready for future use.

EXAMPLE V

A formulation of the compound $F_3$methyl dC suitable for topical administration was prepared by compounding $F_3$methyl dC (0.4 gm) with lanolin (1 gm) as a carrier in a conventional manner to form a cream of smooth consistency, suitable for topical administration.

EXAMPLE VI

A mixture of 5-trifluoromethyl-2'-deoxyuridine ($F_3$dU) (18 g), HMDS (200 ml) and TMCS (1.5 ml) in a Fischer-Porter bottle was pressurized with anhydrous ammonia to 40 psi. The stirred mixture was heated at 65° to 75° C. for 94 hours, giving a pressure of 60 to 70 psi. The excess ammonia was vented off and the excess HMDS was removed under vacuum. Methanol was added to the residue and the mixture was heated to reflux temperature. The methanol was removed under vacuum and the solid residue was recrystallized from water yielding $F_3$methyl dC (7 g) identical to that obtained in Example I.

| Analysis | C | H | N |
|---|---|---|---|
| Actual | 40.72 | 4.23 | 14.36 |
| Theoretical | 40.67 | 4.06 | 14.23 |

COMPARATIVE EXAMPLE A

A mixture of 5-trifluoromethyluracil (0.3), HMDS (5 ml) and TMCS (0.2 ml) in a Fischer-Porter tube was pressurized with anhydrous ammonia to 18 psi. The mixture was heated at 160°–170° C. for 72 hours, giving a pressure of 60 psi. After removal of excess HMDS and hydrolysis of the reaction product with excess methanol under reflux, the starting material (5-trifluoromethyluracil) was recovered. There was no evident (TLC) of other products.

TABLE I
CYTOTOXICITY OF $F_3$METHYL dC vs HEp-2 CELLS

| | | % Survival | | | | | |
|---|---|---|---|---|---|---|---|
| | | −H$_4$U | | | +H$_4$U | | |
| Concentration | mM | .003 | .03 | .3 | .003 | .03 | .3 |
| Experiment | 1 | 3 | <.03 | <.03 | 100 | 57 | <.03 |
| | 2 | 0.1 | 0.0005 | <0.0005 | 93 | 15 | <0.0005 |
| | 3 | 0.1 | 0.0008 | 0.0007 | 53 | 25 | 0.001 |
| | 4 | 0.6 | 0.02 | — | 61 | 31 | — |
| Average %S | | 0.95 | <0.01 | <0.01 | 77 | 32 | <.01 |

H$_4$U concentration:
100 μg/ml in experiment 1 and 2
500 μg/ml in experiment 3 and 4
H$_4$U does not display any cytotoxic activity %S $100 \times \frac{\text{number of cells capable of forming colonies after trypsinization of treated monolayers}}{\text{number of cells capable of forming colonies after trypsinization of untreated monolayers}}$

TABLE II
ANTIVIRAL ACTIVITY OF $F_3$METHYL dC vs HSV-2

| | | Log$_{10}$ Surviving Fraction | | | | | |
|---|---|---|---|---|---|---|---|
| | | −H$_4$U | | | +H$_4$U | | |
| Concentration | mM | .003 | .03 | .3 | .003 | .03 | .3 |
| Experiment | 1 | −0.1 | −3.1 | | −0 | −3.0 | |
| | 2 | −0.92 | −2.7 | −3.7 | −1.5 | −3.7 | −3.7 |
| | 3 | −1.8 | <−4.1 | | −1.9 | <−4.1 | |
| | 4 | | −2.9 | | | −3.7 | |
| Average Log$_{10}$S.F. | | −0.94 | −3.2 | −3.7 | −1.7 | −3.6 | −3.7 |
| %S (from Table I) | | 0.95 | <0.01 | <0.01 | 77 | 32 | <0.01 |

H$_4$U concentration:
100 μg/ml in experiment 1 and 2
500 μg/ml in experiment 3 and 4
H$_4$U does not display any antiviral activity
Log$_{10}$ S.F. = Log$_{10}$Surviving Fraction of Plaque Forming Units Log$_{10}$ $\frac{\text{number of plaques obtained on BHK cell monolayers after plating virus obtained by freezing and thawing treated infected monolayers of HEp-2 cells}}{\text{Number of plaques obtained on BHK cell monolayers after plating virus obtained as above from untreated infected HEp-2 monolayers}}$

TABLE III

CYTOXICITY AND ANTIVIRAL ACTIVITY OF F₃ METHYL dC WITH AND WITHOUT H₄U and 2'dH₄U

|  | No Addition | +H₄U | +2'dH₄U |
|---|---|---|---|
| % S of HEp-2 cells: 0.06 mM | <0.006 | 9 ± 3 | 50 ± 5 |
| Log₁₀S.F. HSV-2: 0.03 mM | −3.3 | −3.4 | −3.5 |
|  | H₄U and 2'dH₄U: | 500 μg/ml |  |

TABLE IV

RELATIONSHIP BETWEEN THE CYTOTOXICITY OF F₃ METHYL dC + H₄U AND ITS ANTIVIRAL ACTIVITY vs HSV-1 AND HSV-2 IN CELL CULTURE

| CONCENTRATION F₃ methyl dC mM | .003 | .03 | .3 |
|---|---|---|---|
| % S | 77 | 32 | <.01 (from Table I) |
| Log₁₀ S.F. vs HSV-2 | −1.7 | −3.6 | −3.7 (from Table II) |
| Log₁₀ S.F. vs HSV-1 | −4.2 | <−4.6 | — (from FIG. 3) |

What is claimed is:

1. A pharmaceutical composition for the treatment of Herpes or Herpes-like viruses, comprising an effective amount of 5-trifluoromethyl-2'-deoxycytidine and an effective amount of a cytidine deaminase inhibitor which is tetrahydrouridine or 2'-deoxytetrahydrouridine.

2. Composition of claim 1, wherein said 5-trifluoromethyl-2'-deoxycytidine is present in said composition in an amount of about 0.01 to 50% by weight.

3. Composition of claim 1, wherein the weight ratio of said cytidine deaminase inhibitor to said 5-trifluoromethyl-2'-deoxycytidine is from about 500:1 to 1:1.

4. Composition of claim 3, in a form suitable for intravenous administration.

5. Composition of claim 3, wherein said 5-trifluoromethyl-2'-deoxycytidine is present in an amount of 0.05 to about 5% by weight.

6. Composition of claim 3, in a form suitable for topical administration.

7. Composition of claim 5, wherein the amount of said 5-trifluoromethyl-2'-deoxycytidine in said composition is about 5 to 50% by weight.

8. Composition of claim 3, in a form suitable for oral administration.

9. Composition of claim 8, wherein said 5-trifluoromethyl-2'-deoxycytidine is present in an amount of about 0.05 to 10% by weight.

10. A method of treating a host suffering from a Herpes or a Herpes-like virus infection, said method comprising administering to said host a therapeutically effective amount of 5-trifluoromethyl-2'-deoxycytidine and a therapeutically effective amount of a cytidine deaminase inhibitor which is tetrahydrouridine or 2'-deoxytetrahydrouridine.

11. Method of claim 10, wherein said inhibitor is administered to the host prior to the administration of said 5-trifluoromethyl-2'-deoxycytidine.

12. A method according to claim 1 wherein the disease is caused by a Herpes Simplex Virus type 1 or 2 or varicella-zoster virus.

13. A method according to claim 10, wherein the 5-trifluoromethyl-2'-deoxycytidine is administered to the host in an amount of about 0.01 to 0.25 mmoles/kg of body weight/day.

14. A method according to claim 13, wherein the 5-trifluoromethyl-2'-deoxycytidine is administered to the host in an amount of about 10 mg/kg body weight/day.

15. Method of claim 14, wherein said cytidine deaminase inhibitor is administered such that the weight ratio of said inhibitor to said 5-trifluoromethyl-2'-deoxycytidine is about 500:1 to 1:1.

* * * * *